US00PP31283P3

(12) United States Plant Patent
Hansen

(10) Patent No.: US PP31,283 P3
(45) Date of Patent: Dec. 24, 2019

(54) ***KNIPHOFIA* PLANT NAMED 'JACKPOT'**

(50) Latin Name: *Kniphofia hybrida*
Varietal Denomination: Jackpot

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 124 days.

(21) Appl. No.: 15/932,742

(22) Filed: Apr. 18, 2018

(65) Prior Publication Data

US 2019/0327876 P1 Oct. 24, 2019

(51) Int. Cl.
*A01H 5/02* (2018.01)
*A01H 6/56* (2018.01)

(52) U.S. Cl.
USPC ..... Plt./443
CPC ..... *A01H 6/56* (2018.05)

(58) Field of Classification Search
USPC ..... Plt./443
CPC ..... A01H 5/02
See application file for complete search history.

*Primary Examiner* — Kent L Bell

(57) ABSTRACT

A new and distinct cultivar of Red Hot Poker plant named *Kniphofia* 'Jackpot' with long, gracefully-arching, strap-like, keeled, glaucous, gray-green foliage and numerous scapes beginning in early summer and repeating though early fall. Habit is densely growing, winter-hardy, tolerant of heat, deer and rabbits. Numerous scapes of vivid reddish-orange flowers on tall scapes beginning in early summer and repeating into early October. The new plant is useful for landscaping as a specimen, en masse, or as a long-lasting cut flower.

2 Drawing Sheets

Botanical classification: *Kniphofia hybrida.*
Variety denomination: 'Jackpot'.

BACKGROUND AND ORIGIN OF THE PLANT

The present invention relates to the new and distinct Red Hot Poker, *Kniphofia* 'Jackpot' hybridized under the direction of the inventor at a wholesale perennial nursery in Zeeland, Mich., USA. The new plant was a single seedling selection resulting from a cross of 'Echo Rojo' U.S. Plant Pat. No. 22,791 as the female parent and 'Papaya Popsicle' U.S. Plant Pat. No. 22,915 as the male parent on Aug. 14, 2012 at the same perennial nursery. The plant passed initial evaluation in the summer of 2014 and was subsequently given the breeder code 12-5-3 prior to naming. *Kniphofia* 'Jackpot' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

No plants of *Kniphofia* 'Jackpot' have been sold, in this country or anywhere in the world, with this name or any other name, prior to the filing of this application, nor has any disclosure of the new plant been made prior to the filing of this application except that which was disclosed within one year of the filing of this application and was either derived directly or indirectly from the inventor.

SUMMARY OF THE PLANT

*Kniphofia* 'Jackpot' differs from its parents as well as all other *Kniphofia* known to the applicant. The most similar known *Kniphofia* cultivars are the female parent 'Echo Rojo', 'Mango Popsicle' U.S. Plant Pat. No. 22,968, the male parent 'Papaya Popsicle', 'Poco Orange' U.S. Plant Pat. No. 27,677 and 'Poker Face' U.S. Plant Pat. No. 30,346. 'Echo Rojo' is slightly shorter in scape height and more reddish in flower color and the new plant is more persistent in the Michigan landscape. 'Mango Popsicle' is much shorter in scape and foliage height with more yellow-orange flower coloration. 'Papaya Popsicle' is significantly shorter in scape and foliage height with slightly more reddish orange flower color. 'Poco Orange' is much smaller in scape height, foliage height and overall habit and has a lighter orange flower color with less red hue. 'Poker Face' is slightly shorter in flower scape and foliage height and the flower color is more orangish hue and less reddish hue.

*Kniphofia* 'Jackpot' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, large-sized clumps.
3. Numerous spikes of vivid reddish-orange flowers on tall stems lightening in maturity;
4. Flowering beginning the first week of summer and repeating into early October in Michigan.

BRIEF DESCRIPTION OF THE DRAWINGS

The photographs of *Kniphofia* 'Jackpot' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
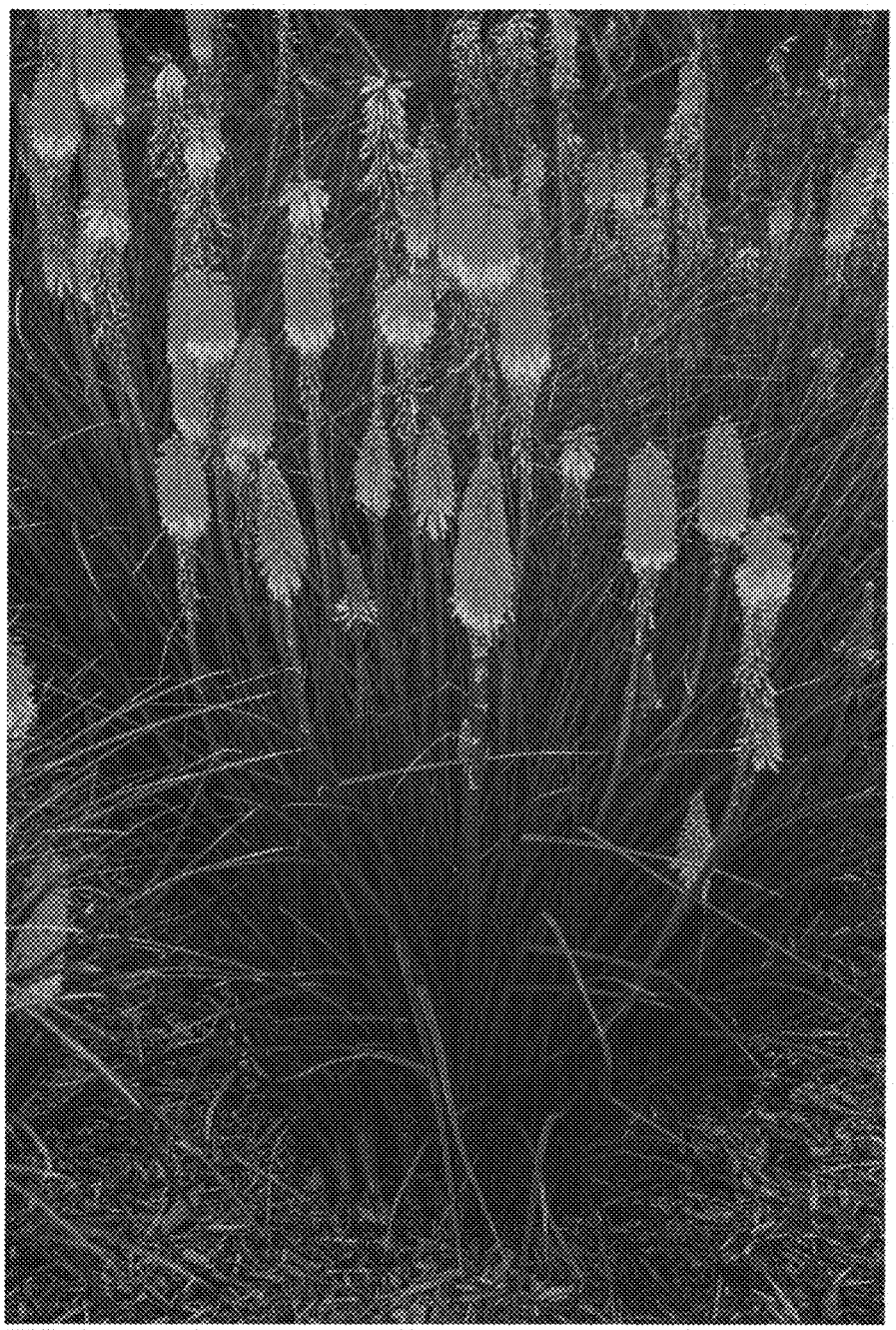
FIG. 1 shows the side-view habit of a five-year-old plant in midseason flowering.
Figure 2:
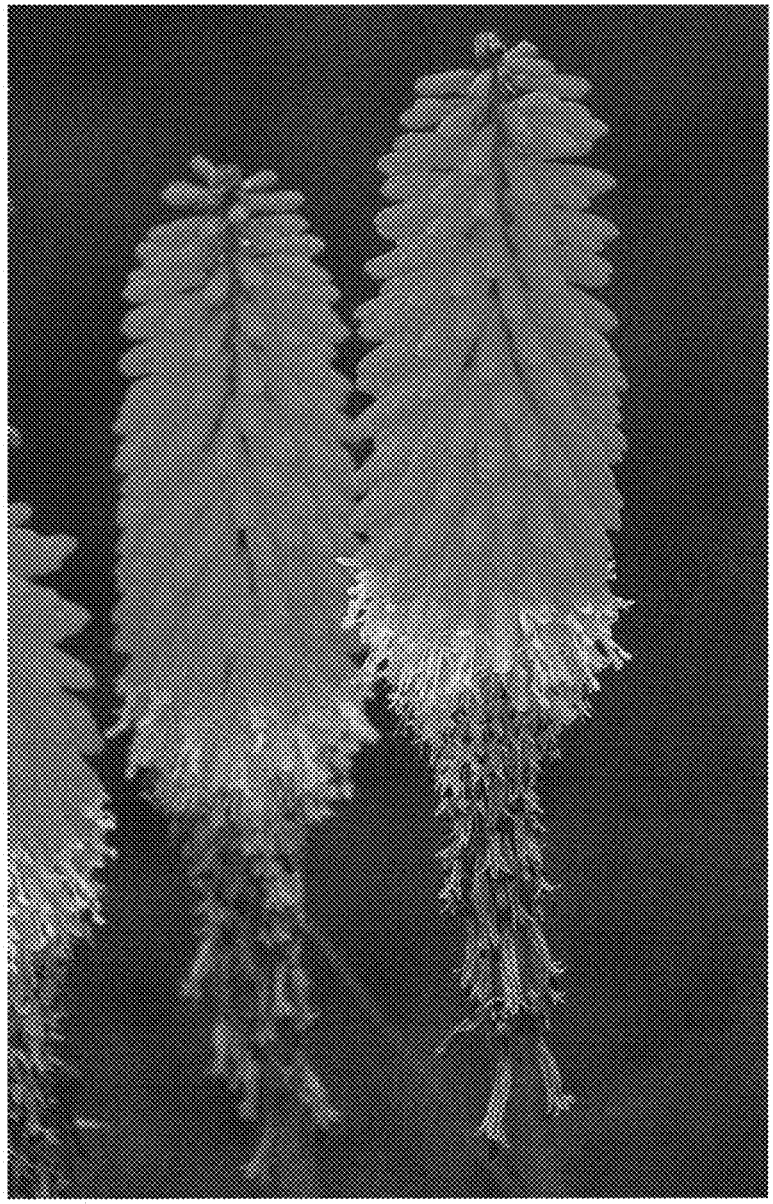
FIG. 2 shows a close-up of the flowers and buds.

The following descriptions and color references are based on the 2015 edition of The Royal Horticultural Society Colour Chart except where common dictionary terms are used. The new plant, *Kniphofia* 'Jackpot', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Echo Rojo' as the female or seed parent and 'Papaya Popsicle' as the male or pollen parent;

Propagation method: By garden division of the rhizome;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 90.0 cm across and about 60.0 cm tall; flowering to about 110.0 cm tall; about 80 peduncles per plant;

Leaves: Linear; keeled at base, triangular in distal half; arranged about 8 leaves per basal division; apex narrowly acute; base tuncate, clasping; margin entire; no fragrance observed;

Leaf size: To about 66.5 cm long and 12.0 mm across at base, average about 60.0 cm long and 10.0 mm across at base;

Leaf color: Young base nearest RHS 158B both abaxial and adaxial, distally nearest RHS 146B both abaxial and adaxial; mature both surfaces between RHS 137A and RBS 137B;

Leaf venation: Parallel; color same as leaf abaxial and adaxial;

Stem: Acaulescent; rhizome about 18.0 mm across at base;

Inflorescence: In spike-like raceme; terete; about 100 flowers per stem; flowering portion to about 27.0 cm tall and about 6.0 cm across; lasting about three weeks; flower spacing less than 1.0 mm apart on raceme in distal region and about 2.5 cm in lowest flowers;

Peduncle: Terete; glabrous; glaucous; solid not fistulose; to about 90.0 cm long and 9.0 mm diameter; average 86.0 cm tall and 8.5 mm diameter;

Peduncle color: Nearest RHS 146D;

Buds one day prior to opening: Ellipsoidal to tubular with swollen subacute apex and rounded base; glabrous; lustrous; about 20.0 mm long and about 3.0 mm diameter at base and 6.0 mm diameter at widest point near apex;

Bud attitude: Beginning outwardly and drooping as maturing toward anthesis;

Bud color: Abaxial distal and dorsal portions between RHS 33A and RHS 33B becoming nearest RHS 24A in ventral with ventral veins nearest RHS N25B;

Flowers: Cylindrical forming tubular corolla; perfect; actinomorphic; individually open and effective about three to four days;

Corolla size: To about 22.0 mm long, fused in basal about 19.0 mm; face to about 8.0 mm tall and about 8.0 mm wide; tube about 3.5 mm diameter near base and about 5.5 mm near throat;

Flower lastingness: Individual flowers last for about 3 to 5 days; inflorescence effective for about 3 weeks as cut flower;

Flower attitude: Drooping;

Flower fragrance: None detected;

Flowering period: Individual racemes effective for about 3 weeks; beginning early summer Michigan for about six weeks, then continuing with repeat racemes until early fall with a short two week break in the heat of the summer;

Tepals: Six, in two sets of three; both sets with acute apices and fused in basal 19.0 mm forming tube; margin entire; glabrous and lustrous abaxial and adaxial; about 22.0 mm long and about 4.0 mm across just above fusion point; inner set with lighter 1.0 mm wide margin;

Tepal color (young abaxial): Distal 3.0 mm of outer tepal set nearest RHS 33B; inner set with 1.0 mm margin of RHS 11D; both sets with midrib nearest RHS 33A and main portion nearest RHS 21D toward base and distally nearest RHS 33B; (young adaxial): distal 3.0 mm of outer tepal set nearest RHS 34B; inner set with 1.0 mm margin nearest RHS NN155; both sets with midrib nearest RHS 28B and main portion proximally nearest RHS 19B and distally between RHS 32C and RHS 32D;

Tepal color (mature abaxial): Both inner and outer sets identically variable between RHS 13C and RHS 15B with nearest RHS 33B near base, inner set with lighter margin of nearest RHS 4D; (mature adaxial): inner and outer sets identical except for inner set with lighter margin nearest RHS 4D; dorsal nearest RHS 15A and ventral nearest RHS 17B with midrib nearest 18A;

Audroecium: Six; variable lengths;

*Filaments.*—Six; exserted; terete; glabrous; lustrous; from about 24.0 to 30.0 mm long and about 0.7 mm diameter; color nearest RHS 1B.

*Anther.*—Slightly flattened ellipsoidal; flattened ventrally to dorsally; about 2.0 mm long and 1.5 mm across and 1.0 mm thick; color nearest RHS 13B.

*Pollen.*—Abundant color nearest RHS 11A.

Gynoecium: Single; about 25.0 mm long;

*Style.*—Terete; glabrous; lustrous; about 22.0 mm long and 0.3 mm diameter: color nearest RHS 1B.

*Stigma.*—Flattened, round; about 0.3 mm across; color nearest RHS 19A.

*Ovary.*—Superior; globose; rounded apex, truncate base; about 2.5 mm long and 2.5 mm diameter; color nearest RHS 144C.

Pedicel: Terete; glabrous; stiff; drooping; about 3.5 mm long and about 1.0 mm diameter;

Pedicel color: Nearest RHS 183B;

Bracts: Lanceolate; at cauline nodes and single bract subtending individual flowers; with acute apices and truncate base; margin entire; dehiscent; to about 11.0 mm long and 5.0 mm across at base; decreasing distally; average about 5.0 mm long and 2.5 mm across; translucent, color blushed with nearest RHS 167B adaxial and abaxial;

Fruit: Tri-valved loculicidal capsule; ellipsoidal; about 6.0 mm long and 4.5 mm across; glabrous; with rounded apex and rounded base; typically five to nine seeded; color upon maturity nearest RHS 200A;

Seed: Irregular with angular sides, acute apex and base; about 4.0 mm long and 2.5 mm across; color nearest RHS 200A;

Disease and pest resistance: 'Jackpot' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct variety of *Kniphofia* plant named 'Jackpot' as herein described and illustrated.

* * * * *